United States Patent [19]

Reinhardt et al.

[11] Patent Number: 4,547,592

[45] Date of Patent: Oct. 15, 1985

[54] THERMOSETTING ARYLETHER COMPOUNDS AND THEIR SYNTHESIS

[75] Inventors: Bruce A. Reinhardt, New Carlisle; Fred E. Arnold, Centerville; Marilyn R. Unroe, Dayton, all of Ohio

[73] Assignee: The United States of America as represented by the Secretary of the Air Force, Washington, D.C.

[21] Appl. No.: 634,346

[22] Filed: Jul. 25, 1984

[51] Int. Cl.[4] ................. C07C 147/06; C07C 43/285; C07C 43/29

[52] U.S. Cl. ..................... 568/33; 525/390; 526/285; 568/29; 568/31; 568/49; 568/333; 568/636; 568/637

[58] Field of Search ............. 568/31, 33, 49, 29, 568/333, 637, 636; 525/390; 526/285

[56] References Cited

U.S. PATENT DOCUMENTS

| | | | |
|---|---|---|---|
| 3,864,309 | 2/1975 | Bilow et al. | 260/47 |
| 4,100,138 | 7/1978 | Bilow et al. | 526/262 |
| 4,108,926 | 8/1978 | Arnold et al. | 528/174 |
| 4,131,625 | 12/1978 | Arnold et al. | 568/33 |
| 4,147,868 | 4/1979 | Arnold et al. | 544/353 |
| 4,263,461 | 4/1981 | Reinhardt et al. | 568/636 |
| 4,268,654 | 5/1981 | Arnold et al. | 526/259 |
| 4,356,325 | 10/1982 | Harrison et al. | 568/33 |
| 4,442,293 | 4/1984 | Tsai et al. | 548/152 |

OTHER PUBLICATIONS

K. Ishizu et al., J. Polymer Sci.: Polymer Chem. Ed., 20, 2851–2862, (1982), New Acetylene-Terminated Quinoxaline Oligomers.

*Primary Examiner*—Mark L. Berch
*Assistant Examiner*—Mary E. Ceperley
*Attorney, Agent, or Firm*—Donald J. Singer; Charles E. Bricker

[57] ABSTRACT

Arylether compounds containing terminal phenylethynyl groups are provided. Also provided is a process for producing these compounds. The following compounds are claimed; 4,4'-bis(3-phenylethynyl-phenoxy) diphenylsulfone; 2,2-bis[([(3-phenoxy]-3-phenoxy)-3-phenylethynyl]-3-phenoxy)-4-phenyl]-propane and 2,2-bis[([(3-phenoxy]-3-phenoxy)-3-phenyl ethynyl]-3-phenoxy)-4-phenyl]-hexafluoropropane.

3 Claims, No Drawings

THERMOSETTING ARYLETHER COMPOUNDS AND THEIR SYNTHESIS

RIGHTS OF THE GOVERNMENT

The invention described herein may be manufactured and used by or for the Government of the United States for all governmental purposes without the payment of any royalty.

FIELD OF THE INVENTION

This invention relates to phenylacetylene-terminated arylether compounds and to their synthesis.

BACKGROUND OF THE INVENTION

Composite materials have been used extensively as structural materials in aerospace and other applications where high strength, lightweight materials capable of withstanding high temperatures are required. Recently, considerable efforts have been made to extend the thermal stability range of these materials, while retaining their good structural strength and without increasing the weight of these materials. Addition polymers such as epoxy resins may be used in conjunction with fillers or fibers to provide essentially void-free composite structures which exhibit good structural properties and are light in weight. These latter structures are, however, limited to temperature applications below about 150°–175° C. because of the thermal stability characteristics of epoxy resins.

In recent years, a number of polymeric materials having high temperature properties have been developed. Unfortunately, the early thermally stable systems in this class of materials were formed by condensation reactions with the evolution of by-products. In the fabrication of reinforced composite structures, the volatile by-products, which were evolved, formed voids in the structures, thereby weakening such structures.

Later developed polymeric systems included ethynyl end-capped oligomers and polymers which propagate and cure by addition reactions to form high molecular weight, thermally stable compositions. Such end-capping has been accomplished in a variety of ways. Bilow et al, U.S. Pat. No. 3,864,309, disclose polyimide oligomers having terminal acetylenic groups which are prepared by the reaction of aromatic dicarboxylic anhydride with 3-aminophenylacetylene. Evers, U.S. Pat. No. 4,147,858 discloses fluorocarbon ether bibenzoxazole oligomers having terminal acetylenic groups which are prepared by the reaction of certain perfluoroalkylene ether diimidate esters and certain perfluoroalkylene ether bis(o-aminophenols) followed by reaction with 2-amino-4-ethynyl-phenol.

Kovar et al, U.S. Pat. No. 3,975,444 disclose that ethynyl-substituted aromatic ortho-diamines are useful as end-capping agents for certain heterocyclic oligomers. Arnold et al, U.S. Pat. Nos. 4,098,825 and Arnold et al 4,108,926 disclose acetylenic end-capping using 3-ethynyl-p-toluene sulfonate.

More recently, the preferred end-capping agent appears to be a substituted terminal acetylene compound containing at least three carbon atoms and a hydroxy group on the carbon atom adjacent to the acetylene group. Arnold et al, U.S. Pat. No. 4,268,654 employ 2-methyl-3-butyn-2-ol as the end-capping agent.

All the above ethynyl-terminated compounds are useful as or in the preparation of thermosetting resins, particularly resins having improved thermo-oxidative stability.

Accordingly, it is an object of the present invention to provide novel arylether compounds containing terminal phenylethynyl groups.

It is another object of the present invention to provide a process for producing novel arylether compounds having terminal phenylethynyl groups.

Other objects and advantages of the present invention will be apparent to those skilled in the art.

DESCRIPTION OF THE INVENTION

In accordance with the present invention there is provided a novel arylether compound having terminal phenylethynyl groups of the general formula

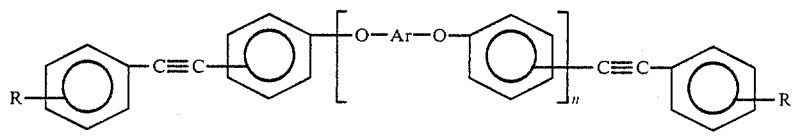

wherein n is an integer having a value of 1–3 and Ar is a divalent aromatic moiety selected from the group consisting of

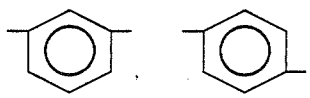

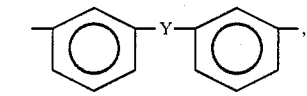

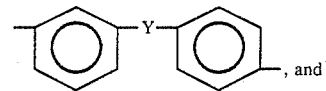

, and

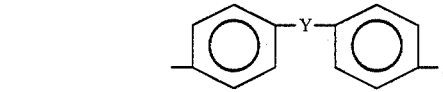

wherein Y is —O—, —S—, —$SO_2$—, —C($CH_3$)$_2$—, —C($CF_3$)$_2$— or —CO—, and wherein R is —H, —O—$C_6H_4$—O—$C_6H_5$ and —O—$C_6H_4$—$SO_2$—$C_6H_5$.

The above compound is prepared by reacting a haloarylether and phenylacetylene or a substituted phenylacetylene in the presence of a catalytic amount of a catalyst system consisting of a substituted phosphine, a complex palladium salt containing two halogen moieties and two substituted phosphine moieties, and a cuprous halide. The substituted phosphine may have substituents selected from the group consisting of phenyl, $C_1$ to $C_4$ alkyl and $C_1$ to $C_4$ alkyl-substituted-phenyl. Examples of suitable phosphines include triphenyl phosphine, triethylphosphine, diphenyl-ethyl phosphine and the like. In the complex palladium salt the halogen is selected from the group consisting of —Br, —Cl and —I, and the substituted phosphine is as defined above. The cuprous halide may be cuprous bromide, cuprous chloride or cuprous iodide.

The haloarylether employed in the present invention has the general formula

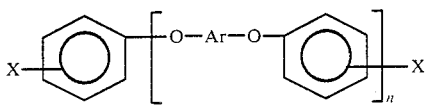

wherein Ar and n are as previously defined and X is a halogen. These haloarylethers may be prepared by an Ullmann ether synthesis, if not otherwise readily available. A suitable preparation is described by Unroe et al, U.S. patent application Ser. No. 522,940, filed Aug. 12, 1983, which is incorporated herein by reference, and involves reacting an aromatic diphenol with a dihalobenzene compound in the presence of cuprous oxide in an Ullman-type condensation in 2,4,6-collidine.

The haloarylether compound and the phenylacetylene or substituted phenylacetylene are reacted in approximately stoichiometric amounts, although an excess of up to about 15 mol% of the acetylenic compound may be employed.

The catalyst system, described previously, is employed in an amount ranging from about 1 to about 10 weight percent of the total weight of reactants. In the catalyst system the relative molar amounts of the Pd complex salt, the substituted phosphine and the cuprous halide can range from about 5:10:1 to about 20:25:1, respectively.

The reaction of the bis-haloarylether with the acetylene terminated compound can be carried out under relatively mild conditions, including a temperature in the approximate range of 20° to 200° C., preferably about 50° to 125° C. Normal reaction pressure is atmospheric, although increased reaction pressures of up to about 250 psig can be employed. The reaction time to employ is somewhat dependent on the particular charge stock and catalyst system chosen and the reaction temperature. In general the reaction time can be from 1 to 150 hours, but is more usually from 3 to 24 hours.

The above reaction is carried out in the presence of a suitable amine solvent. Suitable solvents include dimethylamine, trimethylamine, diethylamine, triethylamine, ethylpropylamine, ethylbutylamine, dibutylamine and the like.

The compounds of this invention can be cured by heating to provide thermally stable compositions having improved thermooxidative properties. The compositions are particularly suitable for use in the fabrication of reinforced composite structures, and for use as high temperature adhesives and coatings.

The following examples illustrate the invention:

EXAMPLE I 1,3-bis-m-(phenylethynyl)phenoxybenzene

A mixture of 6.24 g (0.015 mole) of 1,3-bis-(m-bromophenoxy)benzene and 3.27 g (0.032 mole) of phenylacetylene in 80 ml. of triethylamine was deaerated for 20 minutes by bubbling $N_2$ through the solution. To the deaerated solution was added 0.03 g (0.042 mmol) bis-triphenylphosphine palladium dichloride, 0.30 g (1.14 mmol) of triphenylphosphine and 0.12 g (0.624 mmol) of cuprous iodide. The resulting suspension was heated at reflux for 24 hours under nitrogen. The reaction mixture was cooled to room temperature, then filtered. The triethylamine was removed under reduced pressure to give a brown oil. The oil was purified by column chromatography on silica gel using hexane as the eluent to give 5.1 g of a white solid, mp 78–79. Yield 73.5%.

Analysis: Calc'd for $C_{34}H_{22}O_2$: C, 88.29; H, 4.79. Found: C, 88.58; H, 4.91.

EXAMPLE II 4,4'-bis(3-phenylethynylphenoxy)diphenylsulfone

A solution of 4.0 g (7.1 mmol) of 4,4'-bis(3-bromophenoxy)diphenylsulfone and 1.64 g (16.0 mmol) of phenylacetylene in 100 ml of triethylamine was deaerated for 20 minutes by bubbling nitrogen through the solution. To the deaerated solution was added 0.02 g (0.028 mmol) of bis(triphenylphosphine)Pd dichloride, 0.15 g (0.57 mmol) of triphenyl-phosphine, and 0.05 g (0.26 mmol) of cuprous iodide. The resulting mixture was heated at reflux for 16 hours. The mixture was cooled at RT, filtered and the triethylamine removed under reduced pressure. The resulting oil was purified by column chromatography using 2:1 hexane:methylene chloride as the eluent. The second fluorescent band was collected and the solvent removed under high vacuum to give 2.75 g (64.4%) of a light yellow solid, mp 55° C. (DSC).

Analysis: Calc'd for $C_{40}H_{26}SO_4$: C, 79.71; H, 4.35; S, 5.32. Found: C, 79.91; H, 4.40; S, 5.14.

EXAMPLE III 2,2-bis[([(3-phenoxy]-3-phenoxy)-3-phenylethynyl]-3-phenoxy)-4-phenyl]-propane A mixture of 3.73 g (6.93 mmol) of 2,2-[4,4'-bis(3-bromophenoxy)]diphenylpropane and 4.22 g (14.77 mmol) of 1-phenoxy-(3-ethynylphenoxy)benzene and 0.30 g (1.14 mmol) of triphenylphosphine were dissolved in 75 ml of triethylamine. The solution was stirred under a nitrogen atmosphere for 10 minutes at RT. 0.12 g of cuprous iodide and 0.03 g of bis(triphenylphosphine)Pd dichloride were added to the reaction mixture. The resulting mixture was heated at reflux for 24 hours. The mixture was cooled to RT and the triethylamine was removed under reduced pressure. The residue was washed with methylene chloride and filtered. The filtrate was extracted with 15% HCl (2×100 ml) and washed with water (2×200 ml). After drying over anhydrous magnesium sulfate the solvent was removed to provide a dark brown solid. The crude product was chromatographed on silica gel using 4:1 hexane:methylene chloride. The product was dried in vacuo at 40° C. to afford a light yellow amorphous solid (3.65 g. Yield 56%).

Analysis: Calc'd for $C_{67}H_{48}O_6$: C, 84,81; H, 5.06. Found: C, 85.00; H, 5.29.

EXAMPLE IV 2,2-bis[([(3-phenoxy]-3-phenoxy)-3-phenylethynyl]-3-phenoxy)-4-phenyl]-hexafluoropropane To 125 ml of triethylamine was added 4.9 g (7.6 mmol) of 2,2-bis[3-bromophenoxy)-4-phenyl]hexafluoropropane, 6.5 g (22.8 mmol) of 1-phenoxy-3-(methynylphenoxy)benzene and 0.4 g of triphenylphosphine. The solution was stirred under nitrogen for 10 minutes at RT. 0.2 g of cuprous iodide and 0.2 g of bis(triphenylphosphine)Pd dichloride were added to the reaction mixture. The resulting solution was heated to reflux for 6 hours under a nitrogen atmosphere. The reaction mixture was cooled to RT. The volume of the reaction mixture was reduced and the product was then isolated by filtration. The filtrate was extracted with 15% HCl (2×100 ml) then washed with water (2×200 ml), then dried over anhydrous magnesium sulfate. Removal of the residual solvent afforded 10.35 g of crude product. The product was purified by column chromatography on silica gel using 4:1 hexane:methylene chloride. The product was dried under reduced pressure at 50° C. (5.4 g, Yield 68%)

Analysis: Calc'd for $C_{67}H_{42}O_6F_6$: C, 76.13; H, 3.98. Found: C, 75.93; H, 4.14.

EXAMPLE V

The uncured and cured glass transition temperatures of each of the resins prepared in Examples I–IV are shown in the following Table. The uncured Tg was determined by DSC at a heating rate of 20° C./min. The cured Tg was determined by TMA at a heating rate of 20° C./min. These resins were cured by heating at 300°–312° C. for 8–16 hours.

TABLE

| Resin (Example No.) | Tg (°C.) Uncured | Tg (°C.) Cured |
|---|---|---|
| I | −1 | 246 |
| II | 35 | 177 |
| III | 48 | 105 |
| IV | 16 | 127 |

Various modifications of the present invention may be made in view of the foregoing disclosure without departing from the spirit and scope of the invention.

We claim:
1. The compound 4,4'-bis(3-phenylethynylphenoxy)-diphenylsulfone.
2. The compound 2,2-bis[([(3-phenoxy]-3-phenoxy)-3-phenylethynyl]-3-phenoxy)-4-phenyl]-propane.
3. The compound 2,2-bis[([(3-phenoxy]-3-phenoxy)-3-phenylethynyl]-3-phenoxy)-4-phenyl]-hexafluoropropane.

* * * * *